(12) United States Patent
Ma et al.

(10) Patent No.: US 8,334,110 B2
(45) Date of Patent: Dec. 18, 2012

(54) DETECTION OF BLOOD PLASMA AMYGDALIN OF DISSIPATING BLOOD STASIS BOTANICAL

(75) Inventors: Yueming Ma, Shanghai (CN); Tianming Wang, Shanghai (CN); Yongyu Zhang, Shanghai (CN)

(73) Assignee: Shanghai Sundise Chinese Medicine Technology Development Co., Ltd., Shanghai (CN)

( * ) Notice: Subject to any disclaimer, the term of this patent is extended or adjusted under 35 U.S.C. 154(b) by 460 days.

(21) Appl. No.: 12/451,148

(22) PCT Filed: Apr. 28, 2008

(86) PCT No.: PCT/CN2008/000867
§ 371 (c)(1),
(2), (4) Date: Oct. 27, 2009

(87) PCT Pub. No.: WO2008/131649
PCT Pub. Date: Nov. 6, 2008

(65) Prior Publication Data
US 2010/0173345 A1    Jul. 8, 2010

(30) Foreign Application Priority Data
Apr. 27, 2007   (CN) .......................... 2007 1 0040139

(51) Int. Cl.
C12Q 1/48          (2006.01)
(52) U.S. Cl. .............................. 435/15; 436/63; 436/173
(58) Field of Classification Search .......................... None
See application file for complete search history.

(56) References Cited

U.S. PATENT DOCUMENTS

| 7,989,212 B2 * | 8/2011 | Ma et al. ........................ 436/131 |
| 7,993,928 B2 * | 8/2011 | Ma et al. ........................ 436/63 |
| 2007/0160626 A1 | 7/2007 | Zhang |
| 2010/0093099 A1 | 4/2010 | Ma et al. |
| 2010/0093103 A1 | 4/2010 | Ma et al. |
| 2010/0119541 A1 | 5/2010 | Xu et al. |

FOREIGN PATENT DOCUMENTS

| CN | 1243743 | 2/2000 |
| CN | 99113887.2 | 8/2001 |
| CN | 1472532 | 2/2004 |
| CN | 1669573 | 9/2005 |
| CN | 02136002.2 | 9/2005 |
| CN | 1839996 | 10/2006 |
| CN | 1925864 | 3/2007 |
| CN | 1959409 | 5/2007 |
| CN | 101042380 | 9/2007 |
| CN | 200710040141.6 | 9/2007 |
| CN | 101078712 | 11/2007 |
| CN | 200710040331.8 | 12/2009 |
| CN | 200510028951.0 | 3/2010 |
| JP | 1165583 | 6/1989 |
| WO | 01/41778 | 6/2001 |
| WO | 2004/014409 | 2/2004 |
| WO | 2007/020382 | 2/2007 |

OTHER PUBLICATIONS

Rauws A.G. et al., Determination of amygdalin and its major metabolite prunasin in plasma and urine by high pressure liquid chromatography, Pharmaceutisch Weekblad Scientific Edition, 1982, vol. 4, pp. 172-175.*
Ge B.Y. et al., Identification of amygdalin and its major metabolites in rat urine by LC-MS/MS, Journal of Chromatography B, 2007 (Online 2$^{nd}$ Aug. 2007), vol. 857, pp. 281-286.*
Gaillard Y. et al., Poisoning by plant material: review of human cases and analytical determination of main toxins by high-performance liquid chromatography—(tandem) mass spectrometry, Review, Journal of Chromatography B, (1999), vol. 733, pp. 181-229.*
Dou, et al, "Analysis of Lignans in serum of rats after oral administration of compound Wurenchun capsules by UPLC-MS/MS", Chinese Traditional Patent Medicine, Apr. 2007, vol. 29(4), pp. 550-555.
Yan, et al, "Pharmacokinetics study of schisandrin in Shengmai granule", TraiditonalChinese Drug Research & Clinical Pharmacology, Jan. 2006, vol. 17(1), pp. 36-39.
Liao, et al, "The study in situ on rat intestinal absorption of the active components in GuizhiFuling capsule", Chin. J. Nat. Med., Sep. 2005, vol. 3(5), pp. 303-307.
Xie, et al, "Determinination of anthraquinones and amygdalin in "Taohe Chengqi Decoction", by HPLC", SH. J. TCM, Jul. 2006, vol. 40(7), pp. 73-76.
Pan, et al, "Pharmacokinetics and bioavailability study of danshensu in rat", China Journal of Chinese Materia Medica, Jan. 2008, vol. 33(2), pp. 146-149.
Chen et al, "LC-MS/MS-based measurement of danshen phenolic acids in plasma", Chin. J. Clin Pharmacol Ther, Jul. 2007, vol. 12(7), pp. 748-755.
Tan, et al, "Research Concerning Influence of "Fuzheng Huayu Decoction" on Hepatocellular Apoptosis in Rats with DMN Liver Fibrosis", A Collection of Papers of the 12th National Symposium on Liver Disease with Chinese Integrative Medicine, 2003, pp. 219-223.

(Continued)

Primary Examiner — Jon P Weber
Assistant Examiner — Satyendra Singh
(74) Attorney, Agent, or Firm — Yunling Ren

(57) ABSTRACT

The present invention relates to a determination method of a blood plasma amygdalin of body resistance-strengthening and blood stasis-dissipating botanical composition, comprising the following steps: (1) first adding 2-5 mol/L phosphoric acid to the plasma of mammals administered with the blood stasis-dissipating botanical composition, and mixing to homogenize, the volumetric ratio of plasma to phosphoric acid is 1:2-3, applying the solution to a small column of Waters Oasis HLB activated by methanol and water, after leaching by water and 80-100% methanol and eluting by 0.2-1% ammonia-methanol, drying through evaporation and enriching the eluent at 25-30° C.; and re-dissolving with a mobile phase; (2) UPLC/MS determination method: chromatographic conditions: chromatographic column: Acquity UPLC BEH $C_{18}$, 2.1×100 mm, mobile phase A: Water-Acetonitrile-Formic acid 95:5:0.1 v/v/v, mobile phase B: Acetomtrile-Formic acid 100:0.1 v/v; MS conditions: electrospray ionization (ESI) ion source, detection in the positive ion mode, and the mass scanning range m/z 150~800. The present invention can be used for pharmacokinetic studies of amygdalin of body resistance-strengthening and blood stasis-dissipating botanical composition.

2 Claims, 1 Drawing Sheet

OTHER PUBLICATIONS

Luo et al., "Comparison of schisandrin and schisandrin B in rat serum and plasma after ig Compound Wurenchun Capsules", Chinese Traditional and Herbal Drugs, vol. 37(10), Oct. 2006; pp. 1486-1489.

Xu, et al, "Determination of schizandrin in rat plasma by high-performance liquid chromatography—mass spectrometry and its application in rate pharmacokinetic studies", Journal of Chromatography B, vol. 828, 2005, pp. 55-61.

He, et al, "Analysis of lignan constituents from *Schisandra chinensis* by liquid chromatography—electrospray mass spectrometry", Journal of Chromatography A, vol. 757, 1997, pp. 81-87.

Database Biosis (Online) Biosciences Information Service, Philadelphia, PA, Feb. 2000; Baek Nam-In, et al, "Isolation of anticonvulsant compounds from the fruits of *Schizandra chinensis* Baili" Database accession No. PREV200000198785.

Churchwell, et al, "Improving LC-MS sensitivity through increases in chromatographic performance: Comparisons of UPLC-ES/MS/MS to HPLC-ES/MS/MS", Journal of Chromatography B, vol. 825, 2005, pp. 134-143.

Park, et al, "HPLC Assay and Bioequivalence Evlaution of Biphenyl Dimethyl Dicarboxylate (DDB) Products", J. Liq. Chrom, & Rel. Technol., vol. 21(12), 1998, pp. 1833-1843.

Zhao, et al, "HPLC with Column Switching Coupled to APCI-MS for Pharmacokinetic Study of Amygdalin in Rabbit Plasma", Chromatographia, vol. 65, 2007, pp. 149-153.

Kang, et al, "Micellar electrokinetic chromatography for the analysis of D-amygdalin and its epimer in apricot kernal", Journal of Chromatography A, vol. 866, 2000, pp. 253-259.

Liu, et al, "Effect of Fuzheng Huayu formula and its actions against liver fibrosis", Chinese Medicine, vol. 4(12), 2009, pp. 1-11.

Wang, et al, "Fuzheng Huayu recipe and vitamin E reverse renal interstitial fibrosis through counteracting TGF-B1-induced epithelial-to-mesenchymal transition", Journal of Ethnopharmacology, vol. 127, 2010, pp. 631-640.

Office Action dated Feb. 12, 2010 Issued by the State Intellectual Property Office of the People's Republic of China regarding Application No. 2007100403322.

U.S. Appl. No. 12/451,148, filed Oct. 27, 2009.

European Search Report regarding EP Application No. 08748426.7, Apr. 22, 2010.

European Search Report regarding EP Application No. 08748424.2, Apr. 27, 2010.

* cited by examiner

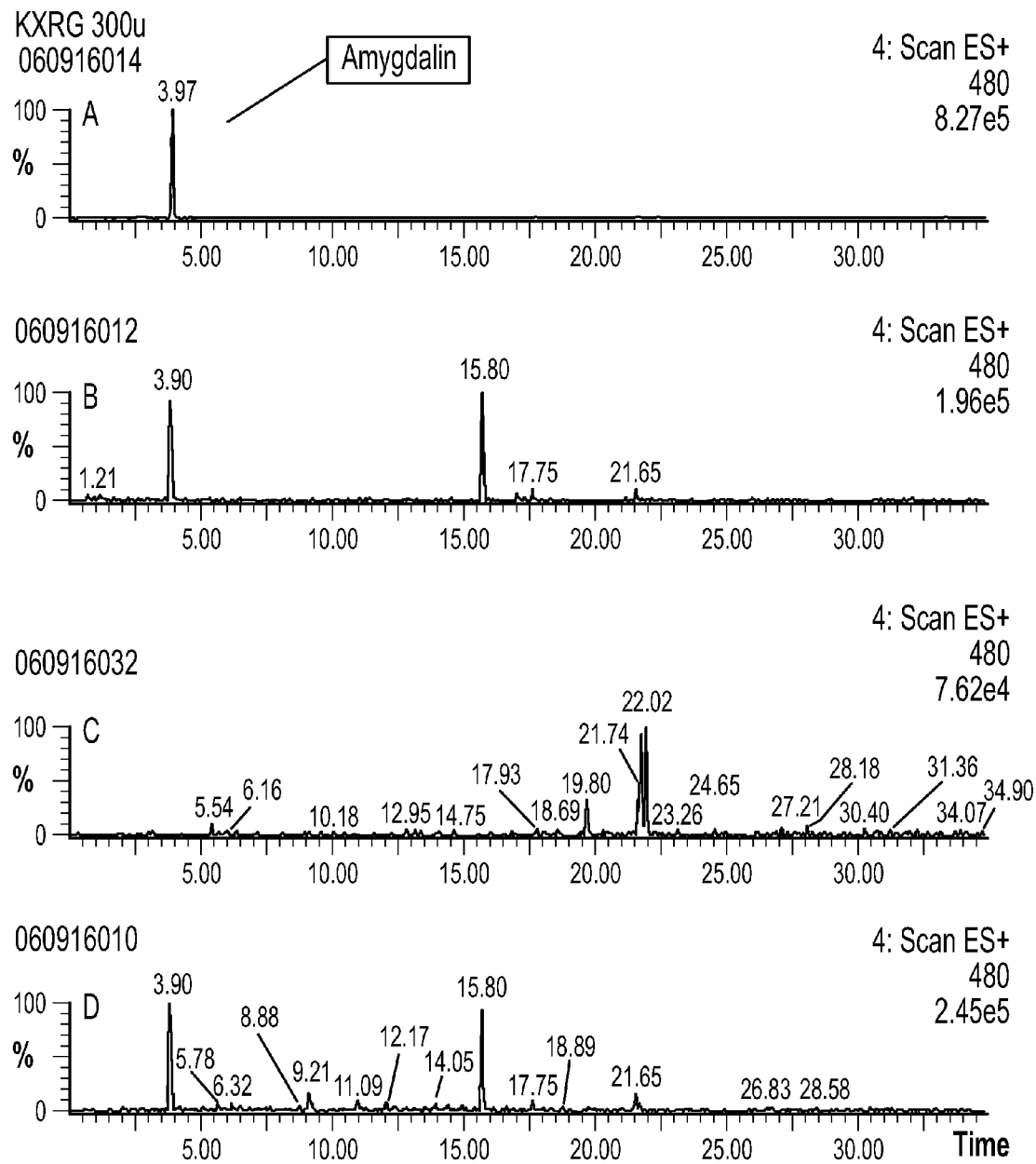

DETECTION OF BLOOD PLASMA AMYGDALIN OF DISSIPATING BLOOD STASIS BOTANICAL

CROSS REFERENCE TO RELATED APPLICATIONS

The present application is a 35 U.S.C. §371 national stage filing of International Patent Application No. PCT/CN2008/000867, filed on Apr. 28, 2008, which claims priority to Chinese Patent Application No. 200710040139.9, filed on Apr. 27, 2007. The disclosures of International Patent Application No. PCT/CN2008/000867 and Chinese Patent Application No. 200710040139.9 are incorporated herein by reference in their entireties.

FIELD OF THE INVENTION

The present invention relates to the pharmacokinetics field, particularly to a determination method of blood plasma Amygdalin of a body resistance-strengthening and blood stasis-dissipating botanical composition.

DESCRIPTION OF THE PRIOR ART

The body resistance-strengthening and blood stasis-dissipating botanical, known as Fuzheng Huayu ("FZHY") composition is a composition prescription composed of "*Salviae miltiorrhizae*, peach kernel, and *Schisandrae chinensis*" etc., which has effect on treating liver, lung and kidney fibrosis; due to the lack of pharmacokinetic research on the body resistance-strengthening and blood stasis-dissipating botanical composition, however, ingredients that are effective in vivo are not clearly understood, making it difficult to control quality and guide rational clinical administration, and consequently hindering the composition from entering the international market.

No relevant pharmacokinetic research reports have so far been found on the body resistance-strengthening and blood stasis-dissipating botanical composition, and there is no method for determining Amygdalin from the composition prescription in biological samples (including blood plasma samples).

SUMMARY OF THE INVENTION

The technical problem that the present invention is to solve is to provide a determination method of blood plasma Amygdalin of the body resistance-strengthening and blood stasis-dissipating botanical composition, and said method is applied for pharmacokinetic research to investigate the pharmacokinetic rules of the blood plasma Amygdalin of the body resistance-strengthening and blood stasis-dissipating botanical composition.

The present invention solves the technical problem through the following technology:

A determination method of blood plasma Amygdalin of the body resistance-strengthening and blood stasis-dissipating botanical composition, comprising the following steps of:

(1) Pretreatment of mammalian blood plasma samples a. After the administration of the body resistance-strengthening and blood stasis-dissipating botanical composition to mammals, first add 2-5 mol/L phosphoric acid to the composition-containing mammalian blood plasma and mix to homogenize, the volumetric ratio of the blood plasma to phosphoric acid is 1:2-3, feed the same to a Waters Oasis HLB cartridge that has been activated by methanol and water, leach with water and 80-100% methanol and elute with 0.2-1% ammonia methanol, then dry through evaporation and enrich the eluent at 25-30° C., and re-dissolve the eluent with a mobile phase;

b. Detection with UPLC-MS method;

(2) UPLC/MS determination method

Chromatographic conditions: chromatographic column: Acquity UPLC BEH $C_{18}$, 2.1×100 mm, mobile phase A: Water-Acetonitrile-Formic acid 95:5:0.1 v/v/v, mobile phase B: Acetomtrile-Formic acid 100:0.1 v/v; MS conditions: electrospray ionization (ESI) ion source, detection in the positive ion mode, and the mass scanning range m/z 150~800.

The ESI ion source in said Step (2) employs detection in the positive ion mode; the desolvation gas flow rate is 440 L/h, the desolvation gas temperature is 300° C., the cone gas flow rate is 50 L/h, the ion source temperature is 100° C., the spray capillary voltage is 3800 V, the sampling cone voltage is 30 V, the extracting cone voltage is 2.00 V, and the lens voltage is 0.1 V. The mass scanning range is m/z 150~800.

In the solid-phase extraction process according to the present invention, the solid phase has an adsorption capacity to the analytes greater than that of the sample mother liquor. When the samples pass through the solid-phase extraction column, the analytes and some similar ingredients are adsorbed to the solid surface, while other ingredients pass through the column with the sample mother liquor. The column is first leached with a solvent having relatively high polarity to rinse and remove a number of unrelated ingredients, the analytes are then eluted with an appropriate solvent, and the eluent is drained and enriched; the analytes are separated from other ingredients in the eluent using a UPLC system, and are finally determined with a MS detector.

Amygdalin in the present invention is a water-soluble ingredient, which can be fully extracted from samples using the solid-phase extraction method. With determination by a UPLC/MS system, moreover, the resolution of Amygdalin from other ingredients in the samples is markedly improved. Furthermore, the analytic method is more sensitive and faster, which facilitates the determination of Amygdalin concentration in blood plasma in pharmacokinetic studies.

BRIEF DESCRIPTION OF THE DRAWINGS

FIG. 1 Amygdalin's UPLC-MS chromatogram. A. Amygdalin; B. Strengthening Body Resistance and Dissipating Blood Stasis Botanical; C. Blank blood plasma; D. Blood plasma of mammals taken 0.5 hours after administration of Strengthening Body Resistance and Dissipating Blood Stasis Botanical.

DETAILED DESCRIPTION OF THE PREFERRED EMBODIMENTS

The present invention will be further described below with reference to specific embodiments. It should be understood that these embodiments are only descriptive rather than restrictive. It should be further understood that after reading the contents taught in the present invention, those skilled in the art could make various changes or modifications to the present invention, while these equivalent forms are similarly encompassed by the scope defined by the appended claims.

Embodiment 1

A determination method of blood plasma Amygdalin of the body resistance-strengthening and blood stasis-dissipating botanical composition, comprising:

1. Pretreatment method of mammalian blood plasma samples: after the administration of a body resistance-strengthening and blood stasis-dissipating botanical composition to mammals, first add 2.17 mol/L phosphoric acid to the composition-containing mammalian blood plasma and mix to homogenize, the volumetric ratio of the biological sample to phosphoric acid is 1:2-3, feed the same to a Waters Oasis HLB cartridge that has been activated by methanol and water, leach with water and 80-100% methanol and elute with 0.2-1% ammonia methanol, then dry through evaporation and enrich the eluent at 25° C., and re-dissolve the eluent with a mobile phase.

2. UPLC/MS determination method: analytical conditions of the UPLC/MS method used in the present invention Chromatographic conditions: chromatographic column: Acquity UPLC BEH $C_{18}$, 2.1×100 mm, mobile phase A: Water-Acetonitrile-Formic acid 95:5:0.1 v/v/v, mobile phase B: Acetonitrile-Formic acid 100:0.1 v/v, eluting according to the following gradient:

| Time (min) | Flow Rate (mL/min) | % A | % B |
|---|---|---|---|
| 0 | 0.300 | 100 | 0 |
| 5.00 | 0.300 | 85.0 | 15.0 |
| 10.00 | 0.300 | 70.0 | 30.0 |
| 20.00 | 0.300 | 40.0 | 60.0 |
| 30.00 | 0.300 | 20.0 | 80.0 |
| 35.00 | 0.300 | 20.0 | 80.0 |
| 35.01 | 0.300 | 100.0 | 0.0 |
| 38.00 | 0.300 | 100.0 | 0.0 |

MS conditions: the electrospray ionization (ESI) ion source employs detection in the positive ion mode; the desolvation gas flow rate is 440 L/h, the desolvation gas temperature is 300° C., the cone gas flow rate is 50 L/h, the ion source temperature is 100° C., the spray capillary voltage is 3800 V, the sampling cone voltage is 30 V, the extracting cone voltage is 2.00 V, and the lens voltage is 0.1 V. The mass scanning range is m/z 150~800.

Determination results: Amygdalin can be detected in the blood plasma of mammals after drenched with a body resistance-strengthening and blood stasis-dissipating botanical composition (see FIG. 1).

The invention claimed is:

1. A method for detecting amygdalin in the blood plasma of an animal after administering a botanical composition comprising Strengthening Body Resistance and Dissipating Blood Stasis Botanical to the animal, comprising the steps of:
   (a) collecting the blood plasma from the animal after the administration of Strengthening Body Resistance and Dissipating Blood Stasis Botanical, wherein said botanical composition comprises *Salviae miltiorrhizae*, peach kernel, and *Schisandrae chinensis*;
   (b) mixing the blood plasma with phosphoric acid with a concentration ranging from 2-5 mol/L at a blood plasma to phosphoric acid volume ratio of 1:2-3 (v/v);
   (c) applying the mixture of step (b) to a chromatography column, wherein the column is pre-activated by methanol and water prior to application of the mixture;
   (d) washing the column with water and 80-100% methanol;
   (e) eluting the column with 0.2-1% ammonia in methanol to obtain an eluent,
   (f) drying the eluent at 25-30° C.;
   (g) dissolving the dried eluent of step (f) in a mobile phase A solution to form a dissolved eluent, wherein the mobile phase A solution comprises water, acetonitrile and formic acid at a water/acetonitrile/formic acid ratio (v/v/v) of 95:5:0.1; and
   (h) separating and detecting amygdalin in the dissolved eluent by ultra performance liquid chromatography/mass spectrometry (UPLC-MS), wherein the UPLC separation conditions comprise separating amygdalin on a 2.1×100 mm, $C_{18}$ UPLC column with an elution gradient comprising the mobile phase A, and the an increasing amount of a mobile phase B, wherein the mobile phase B comprises acetonitrile and formic acid at an acetonitrile/formic acid ratio (v/v) of 100:0.1; and wherein the MS detection conditions comprise electrospray ionization (ESI) ion source detecting in a positive ion mode, and a mass scanning range of m/z 150-800.

2. The method of claim 1, wherein the MS detection step for detecting amygdalin in said dissolved eluent is performed under the conditions comprising: a desolvation gas flow at 440 L/h, a desolvation gas temperature at 300° C., a cone gas flow at 50 L/h, an ion source temperature at 100° C., a spray capillary voltage at 3800 V, a sampling cone voltage at 30 V, an extracting cone voltage at 2.00 V, and a lens voltage at 0.1 V.

* * * * *